(12) United States Patent
Purcell

(10) Patent No.: US 8,912,175 B1
(45) Date of Patent: *Dec. 16, 2014

(54) TOPICAL COMPOSITIONS FOR TREATMENT OF SKIN CONDITIONS

(71) Applicant: Molecular Design International, Inc., Memphis, TN (US)

(72) Inventor: William P. Purcell, Memphis, TN (US)

(73) Assignee: Molecular Design International, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/490,273

(22) Filed: Sep. 18, 2014

Related U.S. Application Data

(60) Division of application No. 13/886,790, filed on May 3, 2013, now Pat. No. 8,865,694, which is a continuation of application No. 11/999,145, filed on Dec. 4, 2007.

(60) Provisional application No. 60/872,528, filed on Dec. 4, 2006.

(51) Int. Cl.
*A61K 31/33* (2006.01)
*A61K 31/60* (2006.01)
*A61K 31/232* (2006.01)
*A61K 8/368* (2006.01)
*A61K 8/37* (2006.01)
*A61K 45/06* (2006.01)
*A61Q 19/08* (2006.01)

(52) U.S. Cl.
CPC .............. *A61K 31/60* (2013.01); *A61K 31/232* (2013.01); *A61K 8/368* (2013.01); *A61K 8/37* (2013.01); *A61K 45/06* (2013.01); *A61Q 19/08* (2013.01)
USPC ......................................... 514/183

(58) Field of Classification Search
USPC ........................................................ 514/183
See application file for complete search history.

(56) References Cited

U.S. PATENT DOCUMENTS

| 4,677,120 A | 6/1987 | Parish et al. |
| 4,885,311 A | 12/1989 | Parish et al. |
| 5,124,356 A | 6/1992 | Purcell et al. |
| 5,605,894 A | 2/1997 | Blank et al. |
| 5,652,266 A | 7/1997 | Bobier-Rival et al. |
| 5,837,728 A | 11/1998 | Purcell |
| 6,168,798 B1 | 1/2001 | O'Halloran et al. |

FOREIGN PATENT DOCUMENTS

| WO | WO 97/30691 | 8/1997 |

OTHER PUBLICATIONS

Leyden, "A Review of the Use of Combination Therapies for the Treatment of *Acne vulgaris*," *Journal of the American Academy of Dermatology*, 2003, vol. 46(3), p. S200-S210.

Varani et al., "MDI 301, A Non-Irritating Retinoid, Induces Changes in Organ-Cultured Human Skin That Underlie Repair," *Arch. Dermatol. Res.* 2007, pp. 439-448, vol. 298.

*Primary Examiner* — Wu-Cheng Winston Shen
*Assistant Examiner* — Christopher R Stone
(74) *Attorney, Agent, or Firm* — Womble Carlyle Sandridge & Rice, LLP

(57) ABSTRACT

The invention provides a topical formulation adapted for treatment of a skin condition comprising (i) at least one retinoid; and (ii) salicylic acid or an ester, amide, salt, or solvate thereof. The invention also includes a kit for treatment of skin conditions comprising a retinoid and salicylic acid, as well as a method of treating skin conditions utilizing the inventive formulation and kit.

12 Claims, No Drawings

TOPICAL COMPOSITIONS FOR TREATMENT OF SKIN CONDITIONS

CROSS-REFERENCE TO RELATED APPLICATIONS

This application is a division of U.S. patent application Ser. No. 13/886,790, filed May 3, 2013, which is a continuation of U.S. patent application Ser. No. 11/999,145, filed Dec. 4, 2007, which claims the benefit of U.S. Provisional Appl. Ser. No. 60/872,528, filed Dec. 4, 2006, which is and the disclosures thereof are hereby incorporated by reference in their entireties.

FIELD OF THE INVENTION

The present invention relates to formulations and kits useful in the treatment of skin conditions. The invention further relates to methods of treatment comprising co-administering multiple active ingredients.

BACKGROUND OF THE INVENTION

Retinoids are a group of compounds known to include retinol (Vitamin A), retinal, all-trans-retinoic acid, 13-cis-retinoic acid, and 9-cis-retinoic acid, as well as a variety of esters and similar derivatives. Many retinoids have useful skin-treatment properties. Vitamin A, for example, has long been employed for dermal treatments, particularly for the treatment of acne in a variety of its manifestations. The use of Vitamin A itself has been limited because of the toxic character of the compound when administered in excess. Vitamin A esters, such as Vitamin A palmitate, for example, are considered safer, although these materials too have substantial levels of toxicity that limits the concentrations at which the compounds can be administered. As a Vitamin A precursor, beta-carotene has also been explored, with the expectation of greater safety. The precursor is less effective, though, since beta-carotene itself is largely inactive and must be cleaved to the active Vitamin A form before the desired effects are produced. Such cleavage, however, is difficult to manage, predict, and control.

Retinal has not achieved such level of dermal use because of the instability of the compound under exposure to heat, oxygen, and ultraviolet light, which makes the compound unacceptable for most candidate uses. All-trans-retinoic acid is generally recognized as the topical product RETIN (Ortho Pharmaceuticals, Inc., a subsidiary of Johnson & Johnson), which has been approved for use in the treatment of acne vulgaris and related forms of acne. A substantial level of administration for other indications has not yet been approved, including anti-wrinkling and antiactinic treatments of the skin. All-trans-retinoic acid has been demonstrated to be irritating to the skin, producing inflammation in a substantial proportion of users. Oral doses of 13-cis retinoic acid, or ACCUTANE® (Roche Dermatologics, a Division of Hoffmann-LaRoche Inc.) have been used in severe cases of cystic acne. The compound is, however, highly teratogenic and mutagenic, and is strictly contraindicated in women of childbearing potential.

A number of retinoids have been identified with antiaging and antiactinic properties, including esters and amides of 13-cis-retinoic acid and all-trans-retinoic acid. In many cases these compounds have activities comparable to the parent acid and comparable inflammatory and irritating characteristics, although some are known to be safer and less irritating than others (sometimes at the expense of reduced effectiveness). Such retinoids have also been shown to be of benefit in the reduction of skin cancers and precancerous lesions of the skin, although to date use for such indications have not been approved by regulatory authorities. Retinol (Vitamin A) and retinoic acid (Vitamin A acid), its isomers, and certain of its analogs are known to have beneficial effects in the treatment of acne and keratinizing skin disorders.

Chronic sun exposure has been determined to create a number of skin disorders including skin cancer, which is usually discernible by the presence of lesions known as keratoses, as well as photoaging (or dermatoheliosis) of the skin, which is characterized by wrinkling, sallowness, roughness and mottled pigmentation. Webb et al, *JAMA* 259, vol. 4, pgs. 527-532, 1988, reported that photoaging of the skin of middle-aged and elderly Caucasians could be improved within a 16-week period by daily topical application of a cream containing 0.1% tretinoin (all-trans-retinoic acid).

Complicating side effects complicating administration of tretinoin include skin irritation and dermatitis of several weeks duration. Thus, a method of dermal therapy that would retain the effectiveness of tretinoin, but which is essentially non-irritating would provide a much needed solution for the treatment of many skin conditions, including acne, psoriasis, photoaging, and the like. In addition, many retinoids require a 10 to 14 day treatment cycle before noticeable therapeutic results are seen. A method of dermal therapy that has a fast onset of treatment effect would be highly desirable.

BRIEF SUMMARY OF THE INVENTION

The present invention provides a safe and effective combination of active agents characterized by synergistic activity, and which is particularly useful in the treatment of skin disorders, particularly acne. The combined active agents include at least one retinoid, particularly selected from a class of retinoids that are non-irritating to skin, and salicylic acid, or an ester, amide, salt, or solvate thereof. The combination of these active ingredients provides a skin treatment formulation characterized by rapid onset of activity and lack of skin irritation.

In one aspect, the invention provides a topical formulation adapted for treatment of a skin condition, the formulation comprising (i) at least one retinoid; and (ii) salicylic acid or an ester, amide, salt, or solvate thereof.

In another aspect, the invention provides a kit for treatment of a skin condition, the kit comprising (i) at least one retinoid in a topical formulation; (ii) salicylic acid or an ester, amide, salt, or solvate thereof in a topical formulation; and (iii) instructions for usage of the kit to treat a skin condition. The retinoid component and the salicylic acid component can be formulated in a single topical formulation or in separate topical formulations.

In yet another aspect, the invention provides a method of treating a skin condition in a subject, comprising topically administering to the subject (i) at least one retinoid, and (ii) salicylic acid or an ester, amide, salt, or solvate thereof. Exemplary skin conditions include acne vulgaris, cystic acne, hyper-pigmentation, hypo-pigmentation, dermal and epidermal hypoplasia and keratoses, wrinkles of the skin as an incident of aging and actinic damage, enlarged pores, surface roughness, ichthyoses, follicular disorders, benign epithelial tumors, perforated dematoses, and disorders of keratinization.

In one embodiment, the retinoid component used in the invention comprises one or more compounds derived from 13-cis-retinoic acid, 13-trans retinoic acid, or 9-cis-retinoic acid (e.g., esters and amides thereof), and wherein the retinoid is characterized by an absence of skin irritation, mutagenicity, and teratogenicity. For example, the retinoid could have either of the following structures:

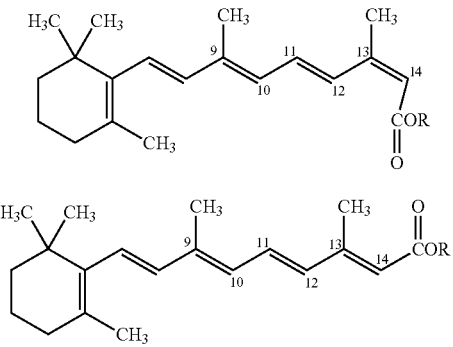

wherein R is:

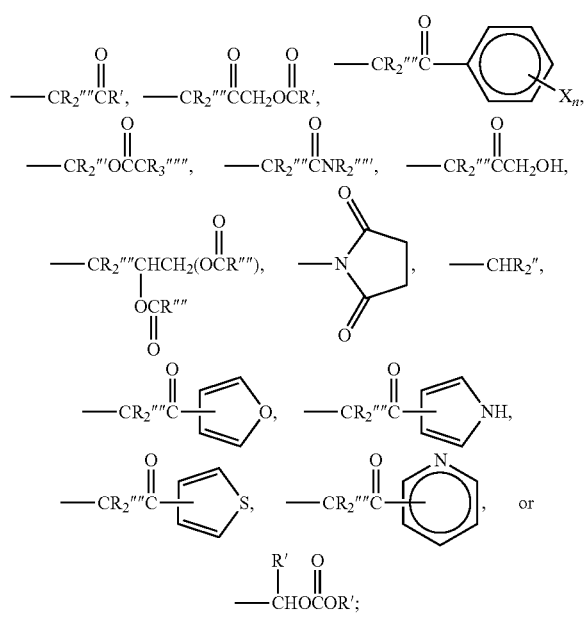

X is —H, —F, —Cl, —Br, —I, —OH, —OR, —OR'

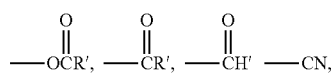

—NO$_2$, —NH$_2$, —NHR', or —NR'$_2$;
n is a number from 1 to 5;
R' is H or any of the lower alkyls ranging from C$_1$ to C$_6$;
wherein R" is

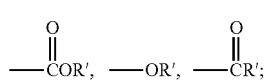

or R';
R'" is the hydrocarbon backbone of fatty acids;
R"" is R' or the hydrocarbon backbone of fatty acids;
R""" is the lower alkyls ranging from C$_1$ to C$_6$; and further, where the are two or more R', R", R'", R"", or R""" groups attached to the same carbon, each R', R", R'", R"", or R""" group may be the same as or different from the other R', R", R'", R"", or R""" groups attached to that carbon.

Alternatively, the retinoid could have either of the following structures:

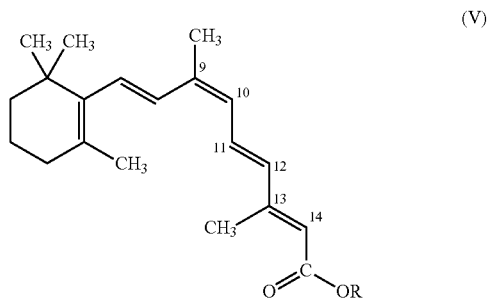

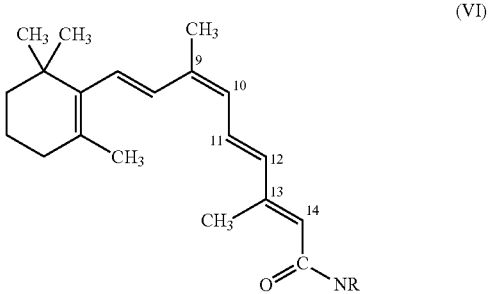

wherein R is:

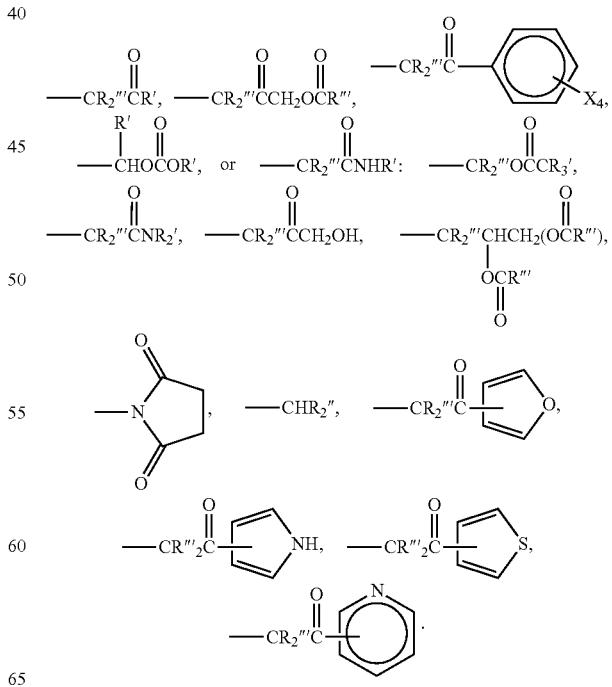

wherein X is —H, —F, —Cl, —Br, —I, —OH, —OR, —OR'

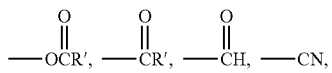

—NO$_2$, —NH$_2$, —NHR', or —NR'$_2$;
wherein n is a number from 1 to 5;
wherein R' is H or any of the lower alkyls ranging from C$_1$ to C$_6$;
wherein R'' is

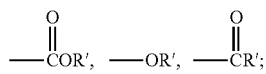

or R';
wherein R''' is the hydrocarbon backbone of fatty acids;
wherein R'''' is R'' or the hydrocarbon backbone of fatty acids;
wherein R''''' is the lower alkyls ranging from C$_1$ to C$_6$; and further,
where the are two or more R', R'', R''', R'''', or R''''' groups attached to the same carbon, each R', R'', R''', R'''', or R''''' group may be the same as or different from the other R', R'', R''', R'''', or R''''' groups attached to that carbon.

Exemplary retinoid compounds for use in the invention include 13-trans retinoic 1-hydroxy-3,3-dimethyl-2-butanone ester, 2-(13-cis-retinoyloxy)-4'-methoxyacetophenone, 1-(13-cis-retinoyloxy)-2-propanone, 1-(13-cis-retinoyloxy)-3-decanoyloxy-2-propanone, 1,3-bis-(13-cis-retinoyloxy)-2-propanone, 2-(13-cis-retinoyloxy)-acetophenone, 13-cis-retinoyloxy methyl 2,2-dimethyl propanoate, 2-(13-cis-retinoyloxy)-n-methyl-acetamide, 1-(13-cis-retinoyloxy)-3-hydroxy-2-propanone, 1-(13-cis-retinoyloxy)-2,3-dioleoylpropanone, succinimdyl 13-cis-retinoate, 1-(13-cis-retinoyloxy) methyl phenyl ketone, 1-(13-cis-retinoyloxy)-2,3-dioleoylpropane, 1-(all-trans-retinoyloxy)-2-propanone, 2-(all-trans-retinoyloxy)-4'-methoxyacetophenone, pinacoyl 9-cis-retinoate, 1-(9-cis-retinoyloxy)-2-propanone, 1-(9-cis-retinoyloxy)-3-decanoyloxy-2-propanone, 1,3-bis-(9-cis-retinoyloxy)-2-propanone, 2-(9-cis-retinoyloxy)-acetophenone, 9-cis-retinoyloxy methyl 2,2-dimethyl propanoate, 2-(9-cis-retinoyloxy)-n-methyl-acetamide, 1-(9-cis-retinoyloxy)-3-hydroxy-2-propanone, 1-(9-cis-retinoyloxy)-2,3-dioleoylpropanone, and succinimidyl 9-cis-retinoate.

In a particularly preferred embodiment, the retinoid is selected from the group consisting of 13-trans retinoic 1-hydroxy-3,3-dimethyl-2-butanone ester, 2-(13-cis-retinoyloxy)-4'-methoxyacetophenone, and pinacoyl 9-cis-retinoate, and the salicylic acid is in the form of an alkali metal salt.

DETAILED DESCRIPTION OF THE INVENTION

The present invention now will be described more fully hereinafter with reference to certain preferred embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The term "alkyl" as used herein means saturated straight, branched, or cyclic hydrocarbon groups. In particular embodiments, alkyl refers to groups comprising 1 to 10 carbon atoms ("C$_{1-10}$ alkyl"). In further embodiments, alkyl refers to groups comprising 1 to 8 carbon atoms ("C$_{1-8}$ alkyl"), 1 to 6 carbon atoms ("C$_{1-6}$ alkyl"), or 1 to 4 carbon atoms ("C$_{1-4}$ alkyl"). In specific embodiments, alkyl refers to methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethybutyl, and 2,3-dimethylbutyl. Substituted alkyl refers to alkyl substituted with one or more moieties selected from the group consisting of halo (e.g., Cl, F, Br, and I); halogenated alkyl (e.g., CF$_3$, 2-Br-ethyl, CH$_2$F, CH$_2$Cl, CH$_2$CF$_3$, or CF$_2$CF$_3$; hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate.

The term "halo" or "halogen" as used herein means fluorine, chlorine, bromine, or iodine.

The term "aryl" as used herein means a stable monocyclic, bicyclic, or tricyclic carbon ring of up to 8 members in each ring, wherein at least one ring is aromatic as defined by the Mickel 4n+2 rule. Exemplary aryl groups according to the invention include phenyl, naphthyl, tetrahydronaphthyl, and biphenyl. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate.

The term "amino" as used herein means a moiety represented by the structure NR$_2$, and includes primary amines, and secondary and tertiary amines substituted by alkyl (i.e., alkylamino). Thus, R$_2$ may represent two hydrogen atoms, two alkyl moieties, or one hydrogen atom and one alkyl moiety.

The terms "alkylamino" and "arylamino" as used herein mean an amino group that has one or two alkyl or aryl substituents, respectively.

The present invention provides useful combinations of compounds beneficial for treating and improving skin conditions and damage to skin. As explained more fully below, the combination of the invention includes at least one retinoid and salicylic acid or an ester, amide, salt, or solvate thereof.

I. Active Agents

The present invention provides combinations of two or more active agents and methods of treatment of various conditions using such combinations. In particular, the combinations are useful in the treatment of damaged skin, such as inflicted wounds (e.g., skin abrasions), acne, photodamage, and age-related skin damage.

A. Retinoids

A variety of retinoids and retinoid derivatives can be used according to the present invention. For example, retinol, retinal, all-trans-retinoic acid, 13-cis-retinoic acid, 13-trans-retinoic acid, and 9-cis-retinoic acid could all be used in the inventive combinations. Particularly beneficial according to certain embodiments of the invention are retinoid derivatives, especially derivatives of 13-cis-retinoic acid, 13-trans retinoic acid, and 9-cis-retinoic acid. The specific deleterious side effect that negatively impact commercialization of many retinoids is skin irritation. Other side effects include mutagenicity and teratogenicity. The preferred retinoids set forth below, such as MDI 101 and MDI 403 (and other esters and amides of 13-cis-retinoic acid, 13-trans-retinoic acid, or 9-cis-retinoic acid), are not irritating to skin, and are also not mutagenic or teratogenic.

Derivatives of 13-cis-retinoic acid and 13-trans-retinoic acid useful in the invention are particularly described U.S. Pat. No. 4,885,311 and U.S. Pat. No. 5,124,356, both of which are incorporated herein by reference. Preferably, the retinoids comprise esters and amides of 13-cis-retinoic acid (Formula I) and 13-trans-retinoic acid (Formula II) having the following structure:

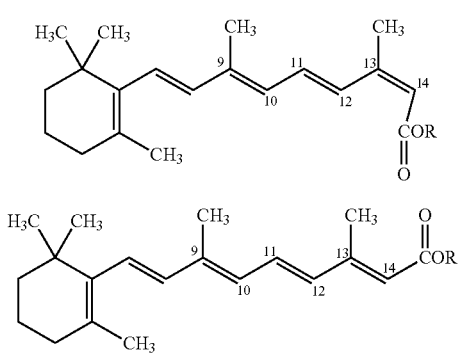

wherein R is:

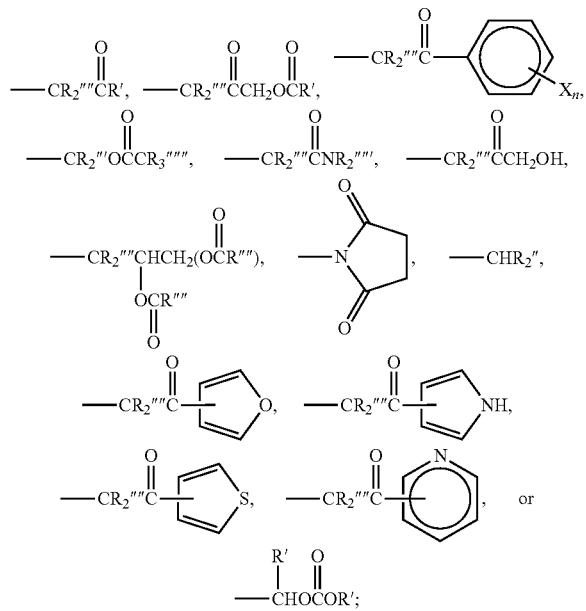

wherein X is —H, —F, —Cl, —Br, —I, —OH, —OR, —OR'

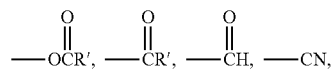

—$NO_2$, —$NH_2$, —NHR', or —$NH'_2$;
wherein n is a number from 1 to 5;
wherein R' is H or any of the lower alkyls ranging from $C_1$ to $C_6$;

wherein R" is

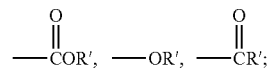

or R';
wherein R''' is the hydrocarbon backbone of fatty acids;
wherein R'''' is R' or the hydrocarbon backbone of fatty acids;
wherein R''''' is the lower alkyls ranging from $C_1$ to $C_6$; and further,
where the are two or more R', R", R''', R'''', or R''''' groups attached to the same carbon, each R', R", R''', R'''', or R''''' group may be the same as or different from the other R', R", R''', R'''', or R''''' groups attached to that carbon.

In certain embodiments, R is preferably —$CH_2C(O)R^a$, wherein $R^a$ is optionally substituted C1-C6 alkyl (e.g., optionally substituted with one or more X groups as defined above), or optionally substituted aryl such as phenyl (e.g., optionally substituted with one or more C1-C6 alkyl groups or X groups as defined above).

In a preferred embodiment, the retinoid derivative used according to the invention is 13-trans retinoic 1-hydroxy-3, 3-dimethyl-2-butanone ester, which is also known as MDI 101 and has the structure according to Formula (III).

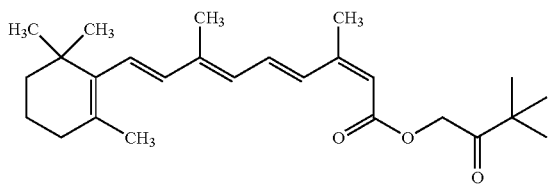

In another preferred embodiment, the retinoid derivative used in the invention is 2-(13-cis-retinoyloxy)-4'-methoxyacetophenone, which is also known as MDI 403 and has the structure according to Formula (IV).

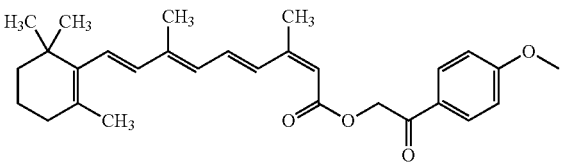

Other exemplary compounds within Formulas (I) or (II) include 1-(13-cis-retinoyloxy)-2-propanone, 1-(13-cis-retinoyloxy)-3-decanoyloxy-2-propanone, 1,3-bis-(13-cis-retinoyloxy)-2-propanone, 2-(13-cis-retinoyloxy)-acetophenone, 13-cis-retinoyloxy methyl 2,2-dimethyl propanoate, 2-(13-cis-retinoyloxy)-n-methyl-acetamide, 1-(13-cis-retinoyloxy)-3-hydroxy-2-propanone, 1-(13-cis-retinoyloxy)-2,3-dioleoylpropanone, succinimdyl 13-cis-retinoate, 1-(13-cis-retinoyloxy) methyl phenyl ketone, 1-(13-cis-retinoyloxy)-2,3-dioleoylpropane, 1-(all-trans-retinoyloxy)-2-propanone, and 2-(all-trans-retinoyloxy)-4'-methoxyacetophenone.

Derivatives of 9-cis-retinoic acid useful in the invention are particularly described U.S. Pat. No. 5,837,728, which is incorporated herein by reference. Preferably, the retinoids comprise esters of 9-cis-retinoic acid (Formula V) and amides of 9-cis-retinoic acid (Formula VI) having the following structure:

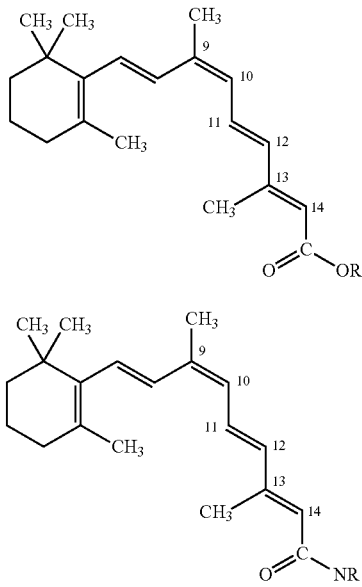

(V)

(VI)

wherein R is:

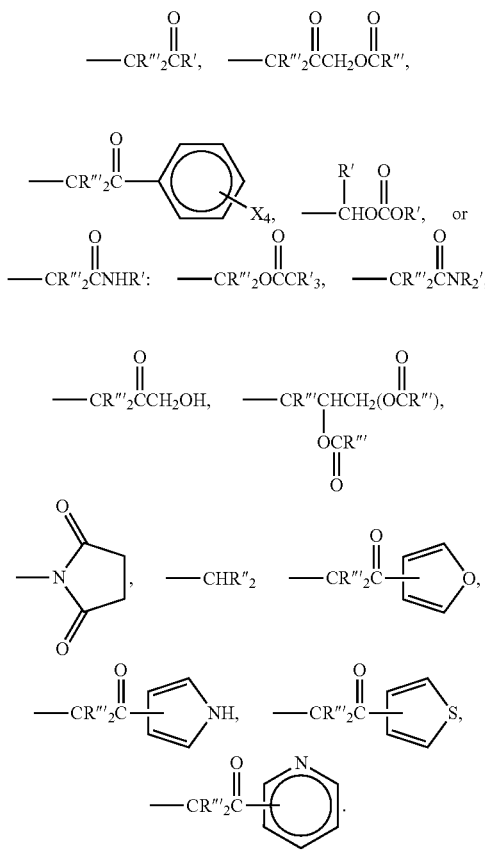

wherein X is —H, —F, —Cl, —Br, —I, —OH, —OR, —OR'

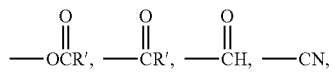

—NO$_2$, —NH$_2$, —NHR', or —NR'$_2$;
wherein n is a number from 1 to 5;
wherein R' is H or any of the lower alkyls ranging from C$_1$ to C$_6$;
wherein R" is

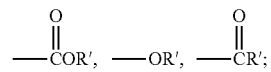

or R';
wherein R''' is the hydrocarbon backbone of fatty acids;
wherein R'''' is R" or the hydrocarbon backbone of fatty acids;
wherein R''''' is the lower alkyls ranging from C$_1$ to C$_6$; and further,
where the are two or more R', R", R''', R'''', or R''''' groups attached to the same carbon, each R', R", R''', R'''', or R''''' group may be the same as or different from the other R', R", R''', R'''', or R''''' groups attached to that carbon.

In a preferred embodiment, the retinoid derivative used according to the invention is pinacoyl 9-cis-retinoate, which is also known as MDI 301 and has the structure according to Formula (VII).

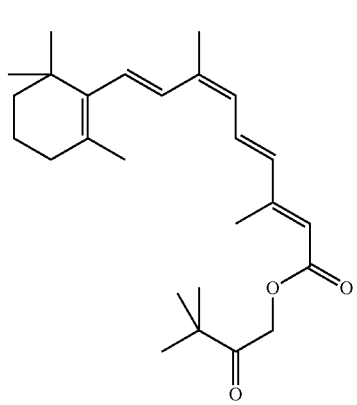

(VII)

Other exemplary compounds within Formulas (V) or (VI) include 1-(9-cis-retinoyloxy)-2-propanone, 1-(9-cis-retinoyloxy)-3-decanoyloxy-2-propanone, 1,3-bis-(9-cis-retinoyloxy)-2-propanone, 2-(9-cis-retinoyloxy)-acetophenone, 9-cis-retinoyloxy methyl 2,2-dimethyl propanoate, 2-(9-cis-retinoyloxy)-n-methyl-acetamide, 1-(9-cis-retinoyloxy)-3-hydroxy-2-propanone, 1-(9-cis-retinoyloxy)-2,3-dioleoyl-propanone, and succinimidyl 9-cis-retinoate. Reference is also made to J. Varani, K. Fay, P. Perone, "MDI 301: a non-irritating retinoid, induces changes in organ-cultured human skin that underlie repair", *Arch. Dermatol. Res.* 298: 439-448 (2007), which is incorporated by reference herein in its entirety.

Retinoids according to the invention are particularly useful in light of their ability to treat acne and similar dermatological disorders. Such compounds are also useful for the non-irritating treatment of skin cancer and photoaging. The use of these compounds also extends to non-irritating treatments involving the retardation and reversal of additional dermatological and cosmetic conditions which are ameliorated by tretinoin such as the effacement of wrinkles, improvement in appearance such as improvement in color or condition of the skin (e.g., reduction in spots caused from exposure to the sun or reduction in surface roughness), as well as other skin disorders such as the decrease or elimination of skin cancers and the retardation of melanoma growth and metastasis.

More specifically, the retinoids of the invention are useful in the treatment of conditions such as acne vulgaris, cystic acne, hyper-pigmentation, hypo-pigmentation, psoriasis, dermal and epidermal hypoplasia and keratoses, the reduction of wrinkling of the skin as an incident of aging and actinic damage, normalization of the production of sebum, the reduction of enlarged pores, promoting the rate of wound healing, limiting of scar tissue formation during healing and the like. They are additionally useful for treatment or amelioration of the same additional classes of skin disorders as is retinoic acid itself and other retinoids. These disorders include ichthyoses (e.g., ichthyosis hystrix, epidermolytic hyperkeratosis, and lamellar ichthyosis), follicular disorders (e.g., pseudofolliculites, senile comedones, nevus comidonicas, and trichostatis spinulosa), benign epithelial tumors (e.g., flat warts, trichoepithelioma, and molluscum contagiosum), perforated dematoses (e.g., elastosis perforans seripiginosa and Kyrles disease), and disorders of keratinization (e.g., Dariers disease, keratoderma, hyperkeratosis plantaris, pityriasis rubra pilaris, lichen planus acanthosis nigricans, and psoriasis).

Retinoid derivatives useful according to the invention can be prepared by conventional methods. For example U.S. Pat. No. 4,677,120 and U.S. Pat. No. 5,124,356, both of which are incorporated herein by reference, disclose methods of synthesizing 13-cis and 13-trans retinoid derivatives. U.S. Pat. No. 5,837,728, which is incorporated herein by reference, discloses methods of synthesizing 9-cis retinoid derivatives. As used herein, "retinoid" refers to all of the above compounds, as well as any biologically active variants, including esters, amides, salts, solvates, or other derivatives thereof.

B. Salicylic Acid

Salicylic acid, also known as 2-hydroxybenzoic acid, is a beta hydroxy acid (BHA) with the formula $C_6H_4(OH)CO_2H$, where the OH group is adjacent to the carboxyl group. Salicylic acid has the structure according to Formula (VIII) below. Alkali metal salts of salicylic acid, such as the sodium salt, are particularly preferred for use in the present invention.

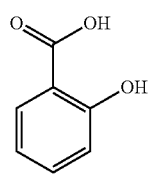

(VIII)

Salicylic acid is the key active ingredient in many skin-care products for the treatment of acne, psoriasis, callulses, corns, keratosis pilaris, and warts. Sodium salicylate also acts as non-steroidal anti-inflammatory drug (NSAID) and induces apoptosis in cancer cells. This active ingredient treats acne by causing skin cells to slough off more readily, thereby preventing clogged pores. This effect on skin cells also makes salicylic acid a useful active ingredient in certain dandruff shampoos. In higher concentrations, salicylic acid is used as a chemical peel. The anti-inflammatory and anesthetic effects of this acid or its salts result in a decrease in the amount of erythema and discomfort that generally is associated with chemical peels. Although the invention includes esters, amides, salts, and solvates of salicylic acid, for ease of reference, salicylic acid is used throughout this disclosure and is understood to include all biologically active variants.

C. Antimicrobial Peptide Component

In some embodiments of the present compositions and methods, the salicylic acid component is replaced with an antimicrobial peptide component. In other embodiments, an antimicrobial peptide component is present in addition to both the retinoid component and the salicylic acid component. This peptide component may be a naturally-occurring or synthetic peptide, or biologically active salt, ester, or other derivative, thereof. The peptide may be glycosylated, phosphorylated, amidated, carboxylated, prenylated, farnesylated, or otherwise modified.

Antimicrobial peptides are produced by numerous organisms, including mammals, birds, reptiles, insects, plants, and microorganisms. Such peptides include cecropins, defensins magainins, cathelicidins, sarcotoxins, and melittin. The peptides tend to be rich in basic amino acids (Lys and Arg) and, therefore, cationic. Some peptides are helical and some amphipathic, having discrete hydrophilic and hydrophobic surfaces. Over 700 different antimicrobial peptide sequences are known. The Department of Biochemistry, Biophysics and Macromolecular Chemistry at the University of Trieste (Italy) maintains a database of antimicrobial peptides. Although widely studied, the mechanism of action of antimicrobial peptides is poorly understood. The peptides appear to cause the formation of pores or channels in membranes, causing membrane depolarization and the loss of essential cellular components.

As examples, U.S. Pat. No. 6,503,881 describes plant and animal-derived cationic peptides that function as indolicidin analogues. U.S. Pat. No. 5,912,230 describes anti-fungal and anti-bacterial histatin-based peptides based on portions of naturally occurring human histatins. U.S. Pat. No. 5,717,064 describes synthetic methylated lysine-rich lytic peptides. U.S. Pat. No. 5,646,014 describes an antimicrobial peptide isolated from silkworm. WO 2004/016653 describes a peptide based on amino acid residues 20-44 sequence of azurocidin. U.S. Pat. No. 6,495,516 and U.S. Pat. Pub. No. 2005/0148495 describe bactericidal peptides based on the bactericidal 55 kDa protein bactericidal/permeability increasing protein (BPI).

U.S. Pat. No. 6,875,744 describes short bioactive peptides containing Phe, Leu, Ala, and Lys residue (i.e., FLAK peptides). The peptides can be used in antibacterial, antifungal, anticancer, and other biological applications. U.S. Pat. Pub. No. 2007/0207112 describes the use of certain FLAK peptides in the preparation of an acne medicament. Several U.S. Patents owned by Demegen, Inc. (Pittsburgh, Pa.) describe lytic peptides containing Phe, Ala, Val, and Lys residues (e.g., U.S. Pat. Nos. 6,559,281, and 6,084,156).

U.S. Pat. Pub. No. 2007/0185019 describes antimicrobial peptides derived from endogenous mammalian proteins, and containing at least four amino acid residues selected from Lys, Arg, and His. WO/2005/014639 describes "periodic" antimicrobial peptides defined by the general formulae: P2N2, P3N, PN2, P2N, and NP, wherein P is a cationic residue (preferably Lys, Arg, or Orn) and N is a hydrophobic residue (preferably Ala, Phe, Gly, Leu, Ile, Thr, Tyr, Trp, Val, or Met).

Preferred antimicrobial peptides for use in the present compositions are synthetic, vegetable-derived, and contain primarily Phe, Ala, Leu, and/or Lys. In some embodiment, the antimicrobial peptide is selected from the peptides described in U.S. Pat. No. 6,875,744 or US 2007/0207112. In one embodiment, the antimicrobial peptide for use in the invention comprises about 15 to about 20 amino acids and at least about 95% of the amino acids are selected from phenylalanine, alanine, leucine, and lysine. All of the references noted herein as directed to antimicrobial peptides are incorporated by reference herein in their entirety.

II. Biologically Active Variants

Biologically active variants of the various compounds disclosed herein as active agents are particularly also encompassed by the invention. Such variants should retain the general biological activity of the original compounds; however, the presence of additional activities would not necessarily limit the use thereof in the present invention. Such activity may be evaluated using standard testing methods and bioassays recognizable by the skilled artisan in the field as generally being useful for identifying such activity.

According to one embodiment of the invention, suitable biologically active variants comprise analogues and derivatives of the compounds described herein. Indeed, a single compound, such as those described herein, may give rise to an entire family of analogues or derivatives having similar activity and, therefore, usefulness according to the present invention. Likewise, a single compound, such as those described herein, may represent a single family member of a greater class of compounds useful according to the present invention. Accordingly, the present invention fully encompasses not only the compounds described herein, but analogues and derivatives of such compounds, particularly those identifiable by methods commonly known in the art and recognizable to the skilled artisan.

The compounds disclosed herein as active agents may contain chiral centers, which may be either of the (R) or (S) configuration, or may comprise a mixture thereof. Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the compounds described herein.

Various methods are known in the art for preparing optically active forms and determining activity. Such methods include standard tests described herein other similar tests which are will known in the art. Examples of methods that can be used to obtain optical isomers of the compounds according to the present invention include the following:

i) physical separation of crystals whereby macroscopic crystals of the individual enantiomers are manually separated. This technique may particularly be used when crystals of the separate enantiomers exist (i.e., the material is a conglomerate), and the crystals are visually distinct;

ii) simultaneous crystallization whereby the individual enantiomers are separately crystallized from a solution of the racemate, possible only if the latter is a conglomerate in the solid state;

iii) enzymatic resolutions whereby partial or complete separation of a racemate by virtue of differing rates of reaction for the enantiomers with an enzyme;

iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis whereby the desired enantiomer is synthesized from an achiral precursor under conditions that produce asymmetry (i.e., chirality) in the product, which may be achieved using chiral catalysts or chiral auxiliaries;

vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;

viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors whereby the desired enantiomer is obtained from non-chiral starting materials and where the stereochemical integrity is not or is only minimally compromised over the course of the synthesis;

x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography whereby the racemate is volatilized and enantiomers are separated by virtue of their differing interactions in the gaseous mobile phase with a column containing a fixed non-racemic chiral adsorbent phase;

xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The compound optionally may be provided in a composition that is enantiomerically enriched, such as a mixture of enantiomers in which one enantiomer is present in excess, in particular to the extent of 95% or more, or 98% or more, including 100%.

The compounds described herein as active agents can be in the form of an ester, amide, salt, or solvate, provided they maintain dermatological activity according to the present invention. Esters, amides, salts, solvates, and other derivatives of the compounds of the present invention may be prepared according to methods generally known in the art, such as, for example, those methods described by J. March, Advanced Organic Chemistry: Reactions, Mechanisms and Structure, 4$^{th}$ Ed. (New York: Wiley-Interscience, 1992), which is incorporated herein by reference.

Examples of dermatologically acceptable salts of the compounds useful according to the invention include acid addition salts. Salts of non-dermatologically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of dermatologically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound useful according to the present invention may be prepared in a similar manner using a dermatologically acceptable base, such as sodium hydroxide, potassium hydroxide, ammonium hydroxide, calcium hydroxide, triethylamine, or the like.

Esters of the active agent compounds according to the present invention may be prepared through functionalization of hydroxyl and/or carboxyl groups that may be present within the molecular structure of the compound. Amides may also be prepared using techniques known to those skilled in the art. For example, amides may be prepared from esters, using suitable amine reactants, or they may be prepared from anhydride or an acid chloride by reaction with ammonia or a lower alkyl amine. Moreover, esters and amides of compounds of the invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0° C. to 60° C. Examples of dermatologically acceptable solvates include, but are not limited to, compounds according to the invention in combination with water, isopropanol, ethanol, methanol, DMSO, ethyl acetate, acetic acid, or ethanolamine.

In the case of solid compositions, it is understood that the compounds used in the methods of the invention may exist in different forms. For example, the compounds may exist in stable and metastable crystalline forms and isotropic and amorphous forms, all of which are intended to be within the scope of the present invention.

If a compound useful as an active agent according to the invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If a compound described herein as an active agent is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum, and lithium.

Reference to any active ingredient herein, such as reference to a retinoid or to salicylic acid, is intended to encompass all biologically active variants of the specific compounds noted herein, including esters, amides, salts, solvates, and other derivatives.

III. Compositions for Topical Administration

While it is possible for individual active agent compounds used in the combinations of the present invention to be administered in the raw chemical form, it is preferred for the compounds to be delivered as part of a composition, such as a cosmetic or dermatological composition. Accordingly, there are provided by the present invention compositions comprising one or more compounds described herein as active agents. As such, the compositions used in the methods of the present invention comprise the active compounds, as described above, or acceptable esters, amides, salts, solvates, analogs, or derivatives thereof.

The active agent compounds described herein can be prepared and delivered together with one or more cosmetically and/or dermatologically acceptable carriers therefore, and optionally, other therapeutic ingredients. Carriers should be acceptable in that they are compatible with any other ingredients of the composition and not harmful to the recipient thereof. A carrier may also reduce any undesirable side effects of the agent. Such carriers or vehicle ingredients are known in the art. See, *Handbook of Cosmetic Science and Technology* Taylor & Francis Group, 2006, herein incorporated by reference in its entirety.

Compositions for topical administration according to the invention can be for local and/or systemic use, depending upon the active ingredient provided therein and the area and frequency of administration. Thus, the following discussion directed to topical formulations could be viewed as describing systemic formulations to the extent an active agent capable of topical systemic administration is included therein.

Compositions for topical administration used in the combinations of the invention can be incorporated into any pharmaceutical, cosmetic, or dermatological preparation customarily used and which may exist in a variety of forms. For example, the composition for topical administration may be a solution, a water-in-oil (W/O) type emulsion, an oil-in-water (O/W) type emulsion, or a multiple emulsion, for example a water-in-oil-in-water (W/O/W) or oil-in-water-in-oil (O/W/O) emulsion, a hydrodispersion or lipodispersion, a gel, a cream, a solid stick, or an aerosol.

Emulsions in accordance with the present invention, for example in the form of a cream, a lotion or a cosmetic milk, are advantageous and comprise, for example, fats, oils, waxes and/or other lipids, as well as water and one or more emulsifiers as they are usually used for such a type of formulation.

In certain embodiments, compositions for topical administration according to the invention may be used, for example, as a protective skin cream, cleansing milk, sun protection lotion, nutrient cream, day cream or night cream and the like, depending on their composition.

The compositions for topical administration may comprise cosmetically active ingredients, cosmetic auxiliaries and/or cosmetic additives conventionally used in such preparations. These include, for example, antioxidants, preservatives, bactericides, thickeners, fillers, antifoams, fragrances, essential oils, pigments (e.g., fumed silica, microfine pigments such as oxides and silicates including optionally coated iron oxide, titanium dioxide, boron nitride, and barium sulfate), ceramides (either as natural materials or functional mimics of natural ceramides), surfactants, emulsifiers, phospholipids, cholesterol, phytosphingosines, additional active ingredients such as vitamins or proteins (e.g., retinyl palmitate or acetate, Vitamin B as panthenol and its derivatives, Vitamin E as tocopheryl acetate, Vitamin F as polyunsaturated fatty acid esters such as gamma-linolenic acid esters), sunscreens (including chemical sunscreens and dispersed physical sunscreens), stabilizers, insect repellents, alcohols, plasticizers, polyols, polymers, foam stabilizers, electrolytes, organic solvents, silicone derivatives, moisturizers and/or humectants, fats, oils, waxes, water, salts, proteolytically or keratolytically active substances, and the like. Such additives can be present in dermatological or cosmetic compositions for topical administration.

As noted above, in addition to the active agent for topical delivery, the topical compositions of the invention can also comprise one or more additional active agents or materials providing a beneficial effect. For example, in specific embodiments, the topical compositions can comprise a sun protection product. These preferably comprise, in addition to the active ingredient used in accordance with the invention, at least one additional UVA filter and/or at least one UVB filter and/or at least one inorganic pigment.

The UVB filters may be soluble in oil or in water. Examples of substances which are soluble in oil are, for example: 3-benzylidenecamphor and its derivatives, for example 3-(4-methylbenzylidene)camphor, 4-aminobenzoic acid derivatives, preferably 2ethylhexyl 4-dimethylaminobenzoate, amyl 4-dimethylaminobenzoate; cinnamic esters, preferably 2-ethylhexyl 4-methoxycinnamate, isopentyl 4-methoxycinnamate; salicylic esters, preferably 2-ethylhexyl salicylate, 4-isopropylbenzyl salicylate, homomenthyl salicylate; benzophenone derivatives, preferably 2-hydroxy-4-methoxybenzophenone, 2-hydroxy-4-methoxy-4'-methylbenzophenone, 2,2'-dihydroxy-4-methoxybenzophenone; benzalmalonic esters, preferably di(2-ethylhexyl) 4-methoxybenzmalonate; 2,4,6-trianilino-(p-carbo-2'-ethyl-1'-hexyloxy)-1,3,5-triazine. Advantageous substances which are soluble in water are: 2-phenylbenzimidazole-5-sulphonic acid and its salts, for example sodium, potassium or triethanolammonium salts, sulphonic acid derivatives of benzophenones, preferably 2-hydroxy-4-methoxybenzophenone-5sulphonic acid and its salts; sulphonic acid derivatives of 3-benzylidenecamphor such as, for example, 4-(2-oxo-3-bornylidene-methyl)benzenesulphonic acid, 2-methyl-5-(2-oxo-3-bornylidenemethyl)sulphonic acid and their salts. Naturally, the list of the abovementioned UVB filters which may be used according to the invention is not intended to be limiting.

Examples of UVA filters that can be used according to the invention include dibenzoylmethane derivatives, in particular 1-(4'-tert-butylphenyl)-3-(4'-methoxyphenyl)propane-1,3-dione and 1-phenyl-3-(4'-isopropylphenyl)propane-1,3-dione.

Examples of inorganic pigments that can be used according to the invention include oxides of titanium, zinc, iron, zirconium, silicon, manganese, aluminum, cerium and mixtures of these, and modifications where the oxides are the active agents. Especially preferably, they are pigments based on titanium dioxide.

Advantageous antioxidants which may be used in accordance with the invention are all those antioxidants which are suitable or conventional for cosmetic and/or dermatological applications. The antioxidants are advantageously selected from the group consisting of amino acids (e.g., glycine, histidine, tyrosine, tryptophan) and their derivatives, imidazoles (e.g., urocaninic acid) and their derivatives, peptides such as D,L-carnosine, D-carnosine, L-carnosine and their derivatives (e.g., anserine), carotenoids, carotenes (e.g., α-carotene, β-carotene, lycopene) and their derivatives, aurothioglucose, propylthiouracil and other thiols (e.g., thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, dilauryl thiodipropionate, distearyl thiodipropionate, thiodipropionic acid and its derivatives (e.g., esters, ethers, peptides, lipids, nucleotides, nucleosides and salts) and sulphoximine compounds (e.g., buthionine sulphoximines, homocysteine sulphoximine, buthionine sulphones, penta-, hexa-, heptathionine sulphoximine) at very low tolerated doses (e.g., pmol to μmol/kg), furthermore (metal)chelating agents (e.g., α-hydroxy fatty acids, palmitic acid, phytic acid, lactoferrin), α-hydroxy acids (e.g., citric acid, lactic acid, malic acid), humic acid, bile acid, bile extracts, bilirubin, biliverdin, EDTA, EGTA and their derivatives, unsaturated fatty acids and their derivatives (e.g., γ-linolenic acid, linolic acid, oleic acid), folic acid and its derivatives, alaninediacetic acid, flavonoids, polyphenols, catechols, ubiquinone and ubiquinol and their derivatives, vitamin C and derivatives (e.g., ascorbyl palmitate, Mg-ascorbyl phosphate, ascorbyl acetate), tocopherols and derivatives (e.g., vitamin E acetate), and coniferyl benzoate of benzoin resin, rutinic acid and its derivatives, ferulic acid and its derivatives, butylhydroxytoluene, butylhydroxyanisole, nordihydroguaiacic acid, nordihydroguaiaretic acid, trihydroxybutyrophenone, uric acid and its derivatives, mannose and its derivatives, zinc and its derivatives (e.g., ZnO, $ZnSO_4$) selenium and its derivatives (e.g., selenium methionine), stilbene and its derivatives (e.g., stilbene oxide, trans-stilbene oxide) and those derivatives of the abovementioned active ingredients which are suitable according to the invention (e.g., salts, esters, ethers, sugars, nucleotides, nucleosides, peptides and lipids).

When provided as solution, emulsion, or dispersion, the compositions for topical administration can comprise solvents exemplified by the following: water or aqueous solutions; oils such as triglycerides of capric or caprylic acid, preferably castor oil; fats, waxes and other natural and synthetic lipids, preferably esters of fatty acids with alcohols of low C number, for example with isopropanol, propylene glycol or glycerol, or esters of fatty alcohols with alkanolic acids of low C number or with fatty acids; alcohols, diols or polyols of low C number and their ethers, preferably ethanol, isopropanol, propylene glycol, glycerol, ethylene glycol, ethylene glycol monoethyl ether or ethylene glycol monobutyl ether, propylene glycol monomethyl ether, propylene glycol monoethyl ether or propylene glycol monobutyl ether, diethylene glycol monomethyl ether or diethylene glycol monoethyl ether, and analogous products. Moreover, mixtures of the abovementioned solvents can be used. In particular reference to alcoholic solvents, water may be a further constituent.

The oil phase of the emulsions, oleogels or hydro- or lipo-dispersions in accordance with the present invention is advantageously selected from the group of the esters of saturated and/or unsaturated, branched and/or unbranched alkanecarboxylic acids with a chain length of 3 to 30 C atoms and saturated and/or unsaturated branched and/or unbranched alcohols with a chain length of 3 to 30 C atoms, from the group of the esters of aromatic carboxylic acids and saturated and/or unsaturated, branched and/or unbranched alcohols with a chain length of 3 to 30 C atoms. In this case, such ester oils may be selected advantageously from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, for example jojoba oil.

Furthermore, the oil phase may advantageously be selected from the group of the branched and unbranched hydrocarbons and hydrocarbon waxes, the silicone oils, the dialkyl ethers, the group of the saturated or unsaturated branched or unbranched alcohols and of the fatty acid triglycerides, viz. the triglycerol esters of saturated and/or unsaturated, branched and/or unbranched alkanecarboxylic acids with a chain length of 8 to 24, in particular 12-18, C atoms. For example, the fatty acid triglycerides may advantageously be selected from the group of the synthetic, semisynthetic and natural oils, for example olive oil, sunflower oil, soya oil, peanut oil, rapeseed oil, almond oil, palm oil, coconut oil, palm kernel oil, and the like. Any mixtures of such oil and wax components may also advantageously be employed in accordance with the present invention. If appropriate, it may also be advantageous to employ waxes, for example cetyl palmitate, as the only lipid component of the oil phase.

The oil phase is advantageously selected from the group consisting of 2-ethylhexyl isostearate, octyldodecanol, isotridecyl isononanoate, isoeicosan, 2-ethylhexyl cocoate, $C_{12-15}$-alkyl benzoate, caprylic/capric acid triglyceride, dicaprylyl ether. Especially advantageous mixtures are those of $C_{12-15}$-alkyl benzoate and 2-ethylhexyl isostearate, those of $C_{12-15}$-alkyl benzoate and isotridecyl isononanoate and those of $C_{12-15}$-alkyl benzoate, 2-ethylhexyl isostearate and isotridecyl isononanoate. In relation to hydrocarbons, liquid paraffin, squalane and squalene may advantageously be used according to the present invention. The oil phase may furthermore advantageously comprise cyclic or linear silicone oils, or consist entirely of such oils, but it is preferred to use an additional content of another oil phase components, apart from the silicone oil(s). Cyclomethicone (octamethylcyclotetrasiloxane) is advantageously employed as silicone oil to be used according to the invention. However, other silicone oils may also be used advantageously in accordance with the present invention, for example hexamethylcyclotrisiloxane, polydimethylsiloxane, poly(methylphenylsiloxane). Especially advantageous mixtures are furthermore those of cyclomethicone and isotridecyl isononanoate and of cyclomethicone and 2-ethylhexyl isostearate.

If appropriate, the aqueous phase of the preparations according to the invention advantageously comprises alcohols, diols or polyols of low C number, and their ethers, preferably ethanol, isopropanol, propylene glycol, glycerol, ethylene glycol, ethylene glycol monoethyl ether or ethylene glycol monobutyl ether, propylene glycol monomethyl ether, propylene glycol monoethyl ether or propylene glycol monobutyl ether, diethylene glycol monomethyl ether or diethylene glycol monoethyl ether and analogous products, furthermore alcohols of low C number, for example ethanol, isopropanol, 1,2-propanediol, glycerol, and, in particular, one or more thickeners which may advantageously be selected from the group consisting of silicon dioxide, aluminum silicates, polysaccharides and their derivatives, for example hyaluronic acid, xanthan gum, hydroxypropylmethylcellulose, especially advantageously from the group of the polyacrylates, preferably a polyacrylate from the group of the so-called Carbopols, for example type 980, 981, 1382, 2984 and 5984 Carbopols, in each case singly or in combination.

Gels used according to the invention usually comprise alcohols of low C number, for example ethanol, isopropanol, 1,2-propanediol, glycerol and water, or an abovementioned oil in the presence of a thickener, which is preferably silicon dioxide or an aluminum silicate in the case of oily-alcoholic gels and preferably a polyacrylate in the case of aqueous-alcoholic or alcoholic gels.

Solid sticks comprise, for example, natural or synthetic waxes, fatty alcohols or fatty acid esters. Customary basic materials which are suitable for use as cosmetic sticks in accordance with the present invention are liquid oils (for example liquid paraffin, castor oil, isopropyl myristate), semi-solid constituents (for example petrolatum, lanolin), solid constituents (for example beeswax, ceresine and microcrystalline waxes, or ozocerite) and waxes of high melting point (for example carnauba wax, candelilla wax).

Suitable propellants for cosmetic and/or dermatological preparations in accordance with the present invention which can be sprayed from aerosol containers are the customary known volatile, liquefied propellants, for example hydrocarbons (propane, butane, isobutane), which may be employed singly or as a mixture with each other. Pressurized air may also be used advantageously. The person skilled in the art will, of course, be familiar with the fact that there are non-toxic propellants, which would be suitable in principle for putting into practice the present invention in the form of aerosol preparations; however, it is recommended to manage without these—in particular fluorohydrocarbons and fluorochlorohydrocarbons (FCHCs)—due to their unacceptable effect on the environment or other accompanying circumstances.

Compositions for topical administration in accordance with the present invention can also be in the form of gels comprising not only an effective amount of active ingredient according to the invention and conventionally used solvents therefor, but also organic thickeners. Example of such thickeners include gum arabic, xanthan gum, sodium alginate, cellulose derivatives, preferably methylcellulose, hydroxymethylcellulose, hydroxyethylcellulose, hydroxypropylcellulose, hydroxypropylmethylcellulose, or inorganic thickeners, for example aluminum silicates such as, for example, bentonites, or a mixture of polyethylene glycol and polyethylene glycol stearate or polyethylene glycol distearate.

An example of an acceptable cosmetic/dermatological formulation containing the above-noted active ingredients can include the following inert ingredients:
Xanthan Gum;
Glycerin 99.7%;
Tetrasodium EDTA;
Glyceryl Stearate and PEG-100 Stearate (ARLACEL® 165);
Cetyl Alcohol;
Isopropyl Palmitate;
Butylated hydroxytoluene (BHT);
Methylparaben;
Propylparaben; and
Deionized Water.

Another example of an acceptable cosmetic/dermatological formulation containing the above-noted active ingredients can include the following inert ingredients:
Steric Acid;
Cetyl Alcohol;
Laureth 4;
CARSONOL® Sles;
Propyl Paraben;
Ascorbyl Palmitate;
Propylene Glycol;
CARBOPOL® 974 P;
Methyl Paraben;
KOH (10%); and
$H_2O$.

The above noted composition can be prepared by a process, for example, as follows:
1. Combine and melt oil phase: Stearic acid, Cetyl Alcohol, Laureth 4, Propyl Paraben, and Ascorbyl Palmitate;
2. In a glass beaker, combine Propylene Glycol and water, disperse Methyl Paraben and CARBOPOL® with high-speed propeller stirring;
3. Add CARSONOL® Sles to product of Step (2);
4. Warm product of Step (3) to 65-70° C.;
5. With mixing, add product of Step (1) to product of Step (4) and mix well;
6. Cool mixture to ~40° C.;
7. Add solvent portion and mix well by hand;
8. Add KOH solution to neutralize; and
9. Protect from light.

IV. Methods of Treatment

The combinations of the invention are useful in the treatment of several conditions described herein evidenced by damaged skin, and the method typically involves topical administration of the formulations of the invention to a mammal, preferably a human. As described above, the retinoid/salicylic acid combination of the invention exhibit useful activities for treating a number of skin conditions. The present invention provides for improved treatment of such conditions by recognizing the ability of these active ingredients to provide a synergistic result. Exemplary skin conditions include acne vulgaris, cystic acne, hyper-pigmentation, hypo-pigmentation, dermal and epidermal hypoplasia and keratoses, wrinkles of the skin as an incident of aging and actinic damage, enlarged pores, surface roughness, ichthyoses (e.g., ichthyosis hystrix, epidermolytic hyperkeratosis, and lamellar ichthyosis), follicular disorders (e.g., pseudofolliculites, senile comedones, nevus comidonicas, and trichostatis spinulosa), benign epithelial tumors (e.g., flat warts, trichoepithelioma, and molluscum contagiosum), perforated dematoses (e.g., elastosis perforans seripiginosa and Kyrles disease), and disorders of keratinization (e.g., Dariers disease, keratoderma, hyperkeratosis plantaris, pityriasis rubra pilaris, lichen planus acanthosis nigracans, and psoriasis).

The retinoids and salicylic acid of the invention typically provide a localized treatment effect through topical application. Accordingly, in certain embodiments, the present invention is directed to methods of treatment comprising co-administering a retinoid and salicylic acid. Note that the composition of the invention, and thus the method of treatment, can include multiple retinoids and/or multiple salicylic acid ingredients (e.g., multiple salicylic acid derivatives). Thus, reference to the combination of a retinoid with salicylic acid is not intended to be limited to merely two active ingredients, but rather encompasses usage of multiple active ingredients within either class of compounds.

In a preferred embodiment, both the retinoid and the salicylic acid are provided in the form of a dermatological or cosmetic composition for topical administration. As used herein, a composition for topical administration is intended to encompass any formulation that can be applied directly to the skin of a patient, particularly to the area of skin suffering from damage that is to be treated.

In specific embodiments, the retinoid component and the salicylic acid component can be combined in a single dosage form, such as a single dermatological or cosmetic composition for topical administration. Alternatively, the two active ingredients can be in separate formulations and simply co-administered to the patient. As used herein, co-administration refers to administration of both active ingredients simultaneously (either together in same formulation or in separate formulations administered at the same time) or administration of the two active ingredients in close temporal proximity to one another. As used herein, the term temporal proximity is intended to mean that administration of the two active ingredients is sufficiently close in time such that the treatment effects provided by the retinoid at least partially overlap with the treatment effects provided by the salicylic acid.

In one embodiment, treatment effective temporal proximity comprises administering the combination such that the intervening time between administration of the retinoid and administration of the salicylic acid is no more than 24 hours. In further embodiments, the combination is administered such that the intervening time between administration of the retinoid and administration of the salicylic acid is no more than 20 hours, no more than 18 hours, no more than 16 hours, no more than 14 hours, no more than 12 hours, no more than 10 hours, no more than 8 hours, no more than 6 hours, no more than 4 hours, no more than 2 hours, no more than 1 hour, no more than 45 minutes, no more than 30 minutes, no more than 15 minutes, no more than 10 minutes, or no more than five minutes. The above time frames defining temporal proximity can be termed "co-administering" the retinoid and the salicylic acid.

In addition to the above, co-administration can also encompass different numbers of administrations of the components over a given time period. For example, the salicylic acid could be administered once per day while the retinoid formulation could be administered multiple times per day. The opposite could also be true. Accordingly, different permutations of administrations of the formulations comprising the combination are encompassed by the invention in line with the dosages described herein.

V. Dosage and Administration

For the treatment of conditions such as described herein, the invention preferably comprises one or more dermatological or cosmetic compositions for topical administration, the compositions comprising a retinoid and salicylic acid. In specific embodiments, the composition is in the form of a lotion, cream, gel, or ointment. Such compositions are applied to areas of damaged skin in need of treatment with a frequency suitable to cause treatment or lessening of the damage being treated. In certain embodiments, the topical composition is applied daily. Specifically, the composition may be applied once daily, twice daily, three times daily, four times daily, or more often as necessary to treat the damaged skin.

Delivery of a therapeutically effective amount of the combination of active ingredients of the invention may be obtained via administration of a therapeutically effective dose of the components of the combination (i.e., the retinoid compound and the salicylic acid compound). Accordingly, in one embodiment, a therapeutically effective amount is an amount effective to treat acne. In one embodiment, the therapeutically effective amount for treating acne is defined as the amount that produces a visible reduction in skin lesions in one week or less following the initiation of treatment. In another embodiment, the therapeutically effective amount is that which produces a visible reduction in skin lesions in three days following the initiation of treatment. In further embodiments, a therapeutically effective amount is an amount effective to treat wound, such as a burn, puncture, cut, or abrasion. In still another embodiment, a therapeutically effective amount is an amount effective to treat skin damage related to age.

The active agents included in the combinations are present in an amount sufficient to deliver to a patient a therapeutic amount of an active ingredient in vivo in the absence of serious toxic effects. The concentration of active agent in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the combinations, and that the dosage ranges set forth herein are exemplary only and are not intended to limit the scope or practice of the combinations.

An effective dose of a compound or composition for treatment of any of the conditions or diseases described herein can be readily determined by the use of conventional techniques and by observing results obtained under analogous circumstances. The effective amount of the compositions would be expected to vary according to the weight, sex, age, and medical history of the subject. Of course, other factors could also influence the effective amount of the composition to be delivered, including, but not limited to, the specific disease involved, the degree of involvement or the severity of the disease, the response of the individual patient, the particular compound administered, the mode of administration, the bioavailability characteristics of the preparation administered, the dose regimen selected, and the use of concomitant medication. The compound is preferentially administered for a sufficient time period to alleviate the undesired symptoms and the clinical signs associated with the condition being treated. Methods to determine efficacy and dosage are known to those skilled in the art. See, for example, Isselbacher et al. (1996) *Harrison's Principles of Internal Medicine* 13 ed., 1814-1882, herein incorporated by reference.

In certain embodiments, a composition for topical administration according to the invention can comprise a retinoid compound in an amount of at least about 0.001% by weight. In further embodiments, the combinations of the invention comprise a retinoid compound in an amount of about 0.001% to about 20% by weight, about 0.01% to about 10% by weight, about 0.01% to about 5% by weight, about 0.01% to about 2.5% by weight, about 0.01% to about 2% by weight, about 0.01% to about 1.5% by weight, about 0.01% to about 1% by weight, about 0.01% to about 0.75% by weight, or about 0.01% to about 0.5% by weight (e.g., about 0.1% by weight, about 0.2% by weight, about 0.3% by weight, about 0.4% by weight, and about 0.5% by weight).

In certain embodiments, a composition for topical administration according to the invention can comprise a salicylic acid compound in an amount of at least about 0.001% by weight. In further embodiments, the combinations of the invention comprise a retinoid compound in an amount of about 0.001% to about 20% by weight, about 0.01% to about 10% by weight, about 0.01% to about 5% by weight, about 0.03% to about 2.5% by weight, about 0.05% to about 2% by weight, about 0.05% to about 1.5% by weight, about 0.05% to about 1% by weight, or about 0.05% to about 0.75% by weight (e.g., about 0.5% by weight, about 0.6% by weight, about 0.7% by weight, about 0.8% by weight, and about 0.9% by weight).

In some embodiments, the antimicrobial peptide component is present in the composition in an amount of at least about 0.001% by weight. In particular embodiments, the antimicrobial peptide component is present in an amount of about 0.001% to about 20% by weight, about 0.001% to about 10% by weight, about 0.001% to about 5% by weight, about 0.001% to about 2.5% by weight, about 0.001% to about 2% by weight, about 0.001% to about 1.5% by weight, about 0.001% to about 1% by weight, or about 0.001% to about 0.75% by weight. Exemplary amounts include about 0.005% by weight, about 0.01% by weight, about 0.05% by weight, about 0.075% by weight, and about 0.1% by weight.

VI. Articles of Manufacture

The present invention also includes an article of manufacture providing a combination as described herein. The article of manufacture can include vials or other containers that contain the combination in forms suitable for use according to the present invention. In particular, the article of manufacture can comprise a kit including one or more containers with a combination according to the invention. In such a kit, the combinations can be delivered in a variety of forms. For example, the combination can be provided as a single dosage form comprising both the retinoic component and the salicylic acid component. Alternately, the combination can be provided as multiple dosage forms, each comprising one or more active ingredients, the dosages being intended for administration in combination, in succession, or in other close proximity of time.

In a specific embodiment, both the retinoid and the salicylic acid can be provided in a form for local, topical application, such as a cream, lotion, or gel, that is provided in a bulk form (i.e., a container including a content of the formulation sufficient for multiple applications) or in a unit dosage form (i.e., a single-use container including a content of the formulation sufficient for a single application, or a single day's applications, to an affected site). The article of manufacture further includes instructions in the form of a label on the container, in the form of an insert included in a box in which the container or containers are packaged, or in the form of a computer readable media, describing a method of treatment. The instructions can also be printed on the box in which the vial or vials are packaged. The instructions contain information such as sufficient dosage and administration information so as to allow the patient or a worker in the field to administer the combination. It is anticipated that a worker in the field encompasses any doctor, nurse, technician, spouse, or other caregiver that might administer the combination. The combination can also be self-administered by the patient.

It is to be understood that while the invention has been described in conjunction with certain preferred specific embodiments thereof, the foregoing description as well as the example that follows are intended to illustrate and not limit the scope of the invention.

Other aspects, advantages and modifications within the scope of the invention will be apparent to those skilled in the art to which the invention pertains.

VII. Experimental

A. Anti-Acne Study of MDI 403

Two groups of 6 male subjects having moderate cases of acne were subjected to a double-blind study wherein each group received one of two treatments. The first treatment (Treatment No. 1) comprised about 0.025% by weight of MDI 403 in a solvent composition comprising about 25% polyethylene glycol 400, about 75% ethanol, and a small amount of BHT. The second treatment (Treatment No. 2) comprised the same formulation as the first treatment with the exception that MDI 403 was replaced with all-trans retinoic acid.

Each subject was instructed to apply the topical treatment once per day at night and to discontinue treatment for one to two days if skin irritation occurs. Each subject was evaluated at the beginning of the study, after one week of treatment, and after two weeks of treatment. The evaluation including counting of the following facial lesions: open comedones, closed comedones, pustules, and papules. Cook's method was used to grade the acne at each evaluation (See Cook, et al. (1979) *Arch. Derm.* 115:571-575).

Tables 1-4 below summarize the percentage reduction at each evaluation point as compared to the baseline evaluation prior to treatment for comedones, pustules, papules, and total acne lesions, respectively. Note that three subjects receiving Treatment No. 2 dropped out of the study within the first seven days due to skin irritation. Accordingly, the data for all-trans retinoic acid is based on a very small sample size and must be evaluated accordingly.

TABLE 1

% REDUCTION IN COMEDONES

| Treatment No. | Days Post Treatment | |
|---|---|---|
|  | 7 | 14 |
| 1 | 12% | 26% |
| 2 | 7% | 47% |

TABLE 2

% REDUCTION IN PUSTULES

| Treatment No. | Days Post Treatment | |
|---|---|---|
|  | 7 | 14 |
| 1 | 8% | 51% |
| 2 | 30% | 54% |

TABLE 3

% REDUCTION IN PAPULES

| Treatment No. | Days Post Treatment | |
|---|---|---|
|  | 7 | 14 |
| 1 | -8% | 11% |
| 2 | -2% | 40% |

TABLE 4

% REDUCTION IN TOTAL ACNE LESIONS

| Treatment No. | Days Post Treatment | |
|---|---|---|
|  | 7 | 14 |
| 1 | 10% | 28% |
| 2 | 8% | 52% |

B. Acne Clinical Trial Using Inventive Formulation

Fifteen panelists exhibiting Grade 2-3 facial acne were recruited for participation in this study. Panelists were randomized into three equal groups corresponding to the three different products they were using: Lotion 1, 2, and 3.

Lotion 1 contained only salicylic acid (0.5% by weight) as an active ingredient. The inactive ingredients were as follows: water, cyclopentasiloxane, dimethyl isosorbide, cetearyl ethylhexanoate, butylene glycol, polysilicone-11, polymethylsilesquioxane, potassium cetyl phosphate, C12-16 alcohols, trimethylol hexyllactone crosspolymer, carnauba wax, fragrance, ceteth-20, glyceryl behenate, hydrogenated lecithin, hydroxyanasatil retinoate, palmitic acid, isohexadecane, ammonium polyacryloyldimethyl taurate, polysorbate 80, sodium cocamidopropyl PG-dimonium chloride phosphate, triethanolamine, caprylyl glycol, phenoxyethanol, hexylene glycol, and BHT.

Lotion 2 contained benzoyl peroxide (2.5% by weight) as the sole active ingredient. The inactive ingredients were as follows: water, cyclomethicone, ethoxydiglycol, propylene glycol, glyceryl stearate, PEG-100 stearate, cetearyl alcohol, dimethicone, panthenol, allantoin, carbomer, ceteareth-20, xanthan gum, triethanolamine, diazolidinyl urea, methylparaben, propylparaben, and fragrance.

Lotion 3 was an exemplary formulation of the invention, containing both salicylic acid (0.5% by weight) and the retinoid MDI 403 (0.3% by weight) as active ingredients. The inactive ingredients were as follows: water, cyclopentasiloxane, dimethyl isosorbide, cetearyl ethylhexanoate, butylene glycol, polysilicone-11, polymethylsilesquioxane, potassium cetyl phosphate, C12-16 alcohols, trimethylol hexyllactone crosspolymer, carnauba wax, fragrance, ceteth-20, glyceryl behenate, hydrogenated lecithin, palmitic acid, isohexadecane, ammonium polyacryloyldimethyl taurate, polysorbate 80, sodium cocamidopropyl PG-dimonium chloride phosphate, triethanolamine, caprylyl glycol, phenoxyethanol, hexylene glycol, and BHT.

The study followed a double blind parallel design. Panelists were required to abstain from using any other topical and/or oral acne treatment during the study and two weeks before the start. On the initial day, the acne condition of each panelist was graded, the number of lesions were counted, and the degree of erythema associated with the acne condition was evaluated. A Minolta Chromameter or the equivalent (SmartProbe 400, IMS Inc.) was used to verify visually-observed erythema instrumentally. Panelists were given instructions to use the product on the acne affected facial areas after cleansing each morning and night at home; and they were provided with a diary to record time of application for the test product together with any comments about product usage.

During each panelist's visit to the lab, on day 3, 7, 14, and 28, counts of visible inflammatory and non-inflammatory lesions associated with the acne condition were conducted, along with scoring of irritation. One (1) adverse reaction was recorded: a small red rash on the entire treatment area of the face was observed Day 13 on a panelist using test product Lotion 2. The reaction disappeared within two days and no additional treatment was required. The panelist was discontinued from further testing.

Inasmuch as every panelist had different baselines in terms of acne counts, the efficacy variables were tabulated in terms of percent improvement relative to baseline (pretreatment condition) and clear, unaffected skin at each evaluation point. The results are summarized in Tables 5-8 below.

TABLE 5

% REDUCTION IN COMEDONES

| Lotion No. | Days Post Treatment | | | |
|---|---|---|---|---|
| | 3 | 7 | 14 | 28 |
| 1 | 2% | 13%* | 23%* | 40%* |
| 2 | 0% | 4% | 15% | 27%* |
| 3 | 2% | 21%* | 39%* | 65%* |

TABLE 6

% REDUCTION IN PAPULES

| Lotion No. | Days Post Treatment | | | |
|---|---|---|---|---|
| | 3 | 7 | 14 | 28 |
| 1 | -16% | 16% | 25% | 31% |
| 2 | 11% | 23% | 48%* | 71%* |
| 3 | 7% | 13% | 13% | 49%* |

TABLE 7

% REDUCTION IN PUSTULES

| Lotion No. | Days Post Treatment | | | |
|---|---|---|---|---|
| | 3 | 7 | 14 | 28 |
| 1 | 41%* | 47%* | 50% | 63%* |
| 2 | 32% | 32% | 53%* | 63%* |
| 3 | 51% | 51% | 51% | 67% |

TABLE 8

% REDUCTION IN TOTAL ACNE LESIONS

| Lotion No. | Days Post Treatment | | | |
|---|---|---|---|---|
| | 3 | 7 | 14 | 28 |
| 1 | 2% | 20%* | 28% | 41%* |
| 2 | 10% | 18% | 37% | 55%* |
| 3 | 16% | 25% | 31%* | 59%* |

While statistically significant reductions in the acne lesion counts were observed for all 3 test products, test material Lotion 3 demonstrated a higher percentage decrease in the total number of lesions observed on days 3 (16%), 7 (25%) and 28 (59%), clearly indicating that Lotion 3 is more effective at improving the acne condition when compared with Lotions 1 and 2.

A faster mechanism of action was also observed at the first evaluation interval for Lotion 3 as compared to the other two tested products. Lotion 3 demonstrated an almost equal degree of activity against non-inflammatory (Table 5, comedones, 65%) and inflammatory (Table 7, pustules, 67%) acne lesions. While test product Lotion 1 did show activity against non-inflammatory (comedones) and inflammatory (pustules) lesions, an increase in the number of inflamed acne lesions (papules) was observed after 3 days (−16%). Lotion 2 performed better in reducing the number of inflammatory (papules and pustules) acne lesions; however, it was the least effective among the three products against non-inflammatory (comedones) lesions and caused an adverse reaction in one test panelist who was discontinued from the study.

Chromameter data indicated that, over a period of 28 days, all three test products improved skin condition by reducing, to some degree, facial skin erythema (a* value) associated with acne and increased skin lightness (L* value). When a* values alone are considered as a function of erythema reduction, changes from clear skin, for all 3 test materials, are apparent but of no considerable difference. However, when integrated with relative light and dark contrast (L* values), Lotion 3 emerged as the product providing the most significant contribution to overall elimination of the appearance of acne, which was corroborated through matched scientific photography and visual analysis. The chromameter data is summarized for each lotion in Tables 9-11 below.

TABLE 9

LOTION 1

| Treatment Day | Clear skin | | Summary - mean | |
|---|---|---|---|---|
| | L* | a* | L* | a* |
| Day 0 | 100.00% | 100.00% | 88.97% | 208.26% |
| Day 3 | | | 90.75% | 202.88% |
| Day 7 | | | 90.53% | 206.11% |
| Day 14 | | | 90.63% | 207.18% |
| Day 28 | | | 91.62% | 198.49% |

TABLE 10

LOTION 2

| Treatment Day | Clear skin | | Summary - mean | |
|---|---|---|---|---|
| | L* | a* | L* | a* |
| Day 0 | 100.00% | 100.00% | 84.46% | 236.67% |
| Day 3 | | | 85.93% | 226.06% |
| Day 7 | | | 86.81% | 221.04% |
| Day 14 | | | 86.15% | 226.70% |
| Day 28 | | | 86.75% | 212.23% |

TABLE 11

| | LOTION 3 | | | |
|---|---|---|---|---|
| | Clear skin | | Summary - mean | |
| Treatment Day | L* | a* | L* | a* |
| Day 0 | 100.00% | 100.00% | 90.33% | 200.42% |
| Day 3 | | | 92.05% | 197.22% |
| Day 7 | | | 91.60% | 199.47% |
| Day 14 | | | 92.03% | 193.41% |
| Day 28 | | | 92.19% | 191.32% |

The experimental results above demonstrate that the combination of a retinoid according to the invention with salicylic acid is effective, safe, non-irritating, and fast-acting. Further, the combination of a retinoid and salicylic acid demonstrated a faster onset of activity against acne and overall better performance than salicylic acid alone or a composition including benzoyl peroxide, the active ingredient in leading acne treatment products such as PROACTIV® solution. The study set forth in Example A confirms that the anti-acne activity of a composition comprising MDI 403 alone is also lower than the exemplary combination of MDI 403 and salicylic acid utilized in Example B at every evaluation point, as evidenced by the percentage reduction of comedones, pustules, papules, and overall acne lesions. In addition, it is clear from the data presented herein that the composition comprising only MDI 403 did not provide significant acne reduction as quickly as the exemplary combination product tested in Example B. Note that Treatment No. 1 in Example A produced a lower percentage reduction of papules, pustules, and total lesions after seven days of treatment than Lotion 3 of Example B produced after only three days of treatment. Accordingly, neither MDI 403 nor salicylic acid, when used singly as an active ingredient in an anti-acne treatment, appears to exhibit an onset of significant anti-acne activity comparable to the inventive formulation used in this study, which demonstrates a synergistic effect attributable to the combination of a retinoid component and a salicylic acid component. Further, the combination of the two active ingredients provided a greater overall anti-acne effect than a treatment comprising benzoyl peroxide, a commercially successful anti-acne ingredient.

That which is claimed:

1. A method for treating a skin condition selected from the group consisting of acne vulgaris, cystic acne, hyper-pigmentation, dermal hypoplasia, epidermal hypoplasia, dermal keratosis, epidermal keratoses, wrinkles of the skin as an incident of aging, enlarged pores, surface roughness, ichthyoses, follicular disorders, benign epithelial tumors, perforated dermatoses, disorders of keratinization, and combinations thereof, comprising topically applying to skin affected by the skin condition a composition comprising:
   (i) at least one active agent according to the structure of Formula (I) or Formula (II)

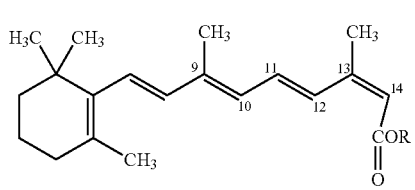

(I)

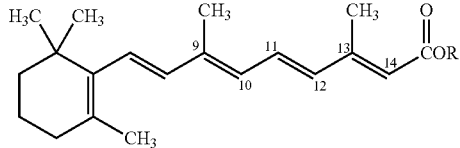

(II)

wherein R is:

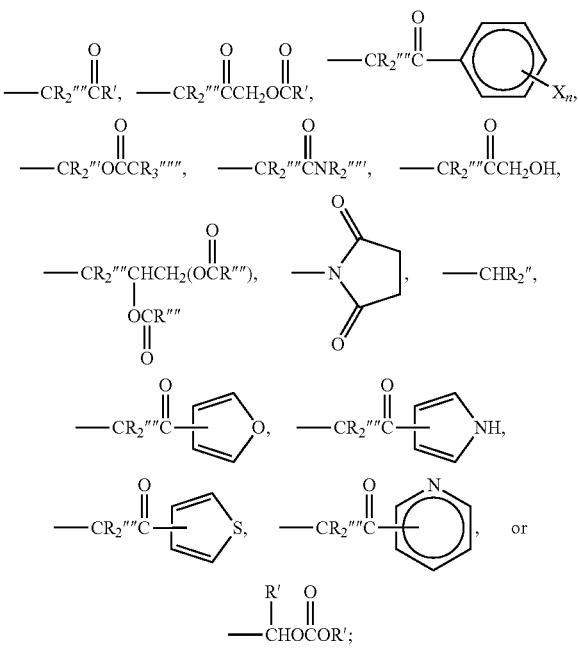

X is —H, —F, —Cl, —Br, —I, —OH, —OR, —OR',

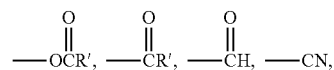

—NO$_2$, —NH$_2$, —NHR', or —NR'$_2$;

n is a number from 1 to 5;

R' is H or any of the lower alkyls ranging from C$_1$ to C$_6$;

wherein R" is

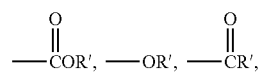

or R';

R''' is the hydrocarbon backbone of fatty acids;

R'''' is R' or the hydrocarbon backbone of fatty acids;

R''''' is the lower alkyls ranging from C$_1$ to C$^6$; and further, where there are two or more R', R", R''', R'''', or R''''' groups attached to the same carbon, each R', R", R''', R'''', or R''''' group may be the same as or different from the other R', R", R''', R'''', or R''''' groups attached to that carbon;

(ii) an active agent according to the structure of Formula (VIII)

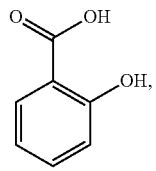
(VIII)

or a salt thereof; and (iii) isohexadecane, polysorbate, phenoxyethanol, one or more C12-C16 alcohols, and one or more polyols.

2. The method according to claim 1, wherein the one or more C12-C16 alcohols comprises cetyl alcohol.

3. The method according to claim 1, wherein the one or more polyols comprises one or both of glycerin and ethoxydiglycol.

4. The method according to claim 1, wherein the composition further comprises one or both of polyethylene glycol (PEG) and xanthan gum.

5. The method according to claim 1, further comprising co-administering a second, different composition that comprises at least one active agent according to the structure of Formula (I) or Formula (II)

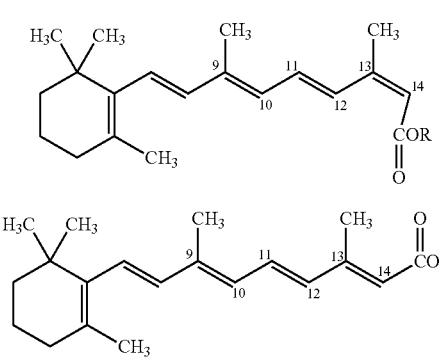
(I)

(II)

wherein R is:

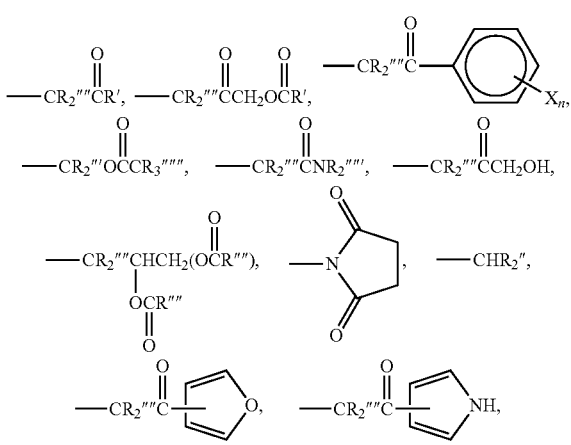

-continued

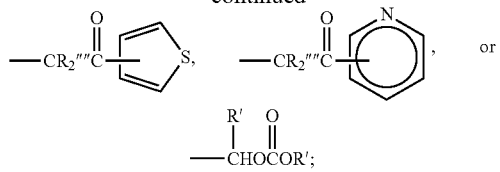

X is —H, —F, —Cl, —Br, —I, —OH, —OR, —OR',

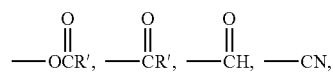

—$NO_2$, —$NH_2$, —NHR', or —$NR'_2$;
n is a number from 1 to 5;
R' is H or any of the lower alkyls ranging from $C_1$ to $C_6$;
wherein R'' is

—COR', —OR', —CR', or R';
R''' is the hydrocarbon backbone of fatty acids;
R'''' is R' or the hydrocarbon backbone of fatty acids;
R''''' is the lower alkyls ranging from $C_1$ to $C^6$; and further, where there are two or more R', R'', R''', R'''', or R''''' groups attached to the same carbon, each R', R'', R''', R'''', or R''''' group may be the same as or different from the other R', R'', R''', R'''', or R''''' groups attached to that carbon.

6. The method according to claim 5, wherein said co-administration comprises sequential administration in any order.

7. The method according to claim 5, wherein the second composition comprises a cleanser.

8. The method according to claim 5, wherein the second composition comprises a moisturizer.

9. A composition adapted for topical administration to the skin, the composition comprising:
(i) one or more of: 13-trans retinoic 1-hydroxy-3,3-dimethyl-2-butanone ester; 2-(13-cis-retinoyloxy)-4'-methoxyacetophenone; and pinacoyl 9-cis-retinoate;
(ii) an active agent according to the structure of Formula (VIII)

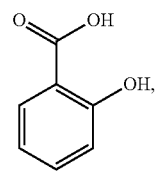
(VIII)

or a salt thereof;
(iii) one or more C12-C16 alcohols;
(iv) one or more polyols;
(v) a polysorbate; and
(vi) one or more of isohexadecane, polyoxyethanol, polyethylene glycol (PEG), and xanthan gum.

10. The composition according to claim 9, wherein the one or more C12-C16 alcohols comprises cetyl alcohol.

11. The composition according to claim 9, wherein the one or more polyols comprises one or both of glycerin and ethoxydiglycol.

12. A kit comprising at least two containers that separately include different compositions adapted for topical administration, wherein:
   (i) one of the at least two containers includes a composition according to claim 9;
   (ii) one of the at least two containers includes a composition that comprises a cleanser or a moisturizer; and
   (iii) the kit includes a set of instructions containing dosage and administration information instructing a user regarding sequential administration of the different compositions in the at least two containers.

* * * * *